(12) United States Patent
Reddy et al.

(10) Patent No.: US 11,274,081 B2
(45) Date of Patent: Mar. 15, 2022

(54) PROCESS FOR THE SYNTHESIS OF IVACAFTOR

(71) Applicant: COUNCIL OF SCIENTIFIC & INDUSTRIAL RESEARCH, Delhi (IN)

(72) Inventors: Dumbala Srinivasa Reddy, Maharashtra (IN); Amol Arvind Kulkarni, Maharashtra (IN); Vasudevan Natarajan, Maharashtra (IN); Mrityunjay Keshavprasad Sharma, Maharashtra (IN)

(73) Assignee: COUNCIL OF SCIENTIFIC & INDUSTRIAL RESEARCH, Delhi (IN)

( * ) Notice: Subject to any disclaimer, the term of this patent is extended or adjusted under 35 U.S.C. 154(b) by 402 days.

(21) Appl. No.: 16/305,280

(22) PCT Filed: May 26, 2017

(86) PCT No.: PCT/IN2017/050203
§ 371 (c)(1),
(2) Date: Nov. 28, 2018

(87) PCT Pub. No.: WO2017/208253
PCT Pub. Date: Dec. 7, 2017

(65) Prior Publication Data
US 2020/0325104 A1    Oct. 15, 2020

(30) Foreign Application Priority Data
May 30, 2016   (IN) .............................. 201611018491

(51) Int. Cl.
*C07D 215/56*   (2006.01)
(52) U.S. Cl.
CPC .................................. *C07D 215/56* (2013.01)

(58) Field of Classification Search
CPC ...................................................... C07D 215/56
See application file for complete search history.

(56) References Cited

U.S. PATENT DOCUMENTS

| 7,495,103 | B2 | 2/2009 | Hadida-Ruah et al. |
| 2010/0267768 | A1 | 10/2010 | DeMattei et al. |
| 2011/0064811 | A1 | 3/2011 | Hurter et al. |
| 2011/0230519 | A1 | 9/2011 | Arekar et al. |

FOREIGN PATENT DOCUMENTS

| WO | WO 2007/079139 A2 | 7/2007 |
| WO | WO 2014/118805 A1 | 8/2014 |
| WO | WO 2014/125506 A2 | 8/2014 |
| WO | WO 2016/181414 A1 | 11/2016 |

OTHER PUBLICATIONS

BATCHO. Organic Syntheses, 1985, 63, 214 (Year: 1985).*
International Search Report for related International Application No. PCT/IN2017/050203 dated Sep. 26, 2017.
N. Vasudevan et al.; "Breaking and Making of Rings: A Method for the Preparation of 4-Quinolone-3-carb-oxylic Acid Amides and the Expensive Drug Ivacaftor", European Journal of Organic Chemistry, Nov. 3, 2015, pp. 7433-7437.

* cited by examiner

*Primary Examiner* — Noble E Jarrell
(74) *Attorney, Agent, or Firm* — Renner, Otto, Boisselle & Sklar, LLP

(57) ABSTRACT

The present disclosed an improved process for the synthesis of ivacaftor starting from indole acetic acid ester which can be performed in batch as well as continuous flow synthesis. The present invention further disclosed to a continuous process for the synthesis of compound of formula (II) or formula (III) from compound of formula (I) in continuous flow reactor.

18 Claims, 2 Drawing Sheets

PROCESS FOR THE SYNTHESIS OF IVACAFTOR

FIELD OF THE INVENTION

The present invention relates to a process for the synthesis of ivacaftor. More particularly, the present invention relates to an improved process for the synthesis of ivacaftor starting from indole acetic acid ester which can be performed in batch as well as continuous flow synthesis. The present invention further relates to a continuous process for the synthesis of compound of formula (II) or formula (III) from compound of formula (I) in continuous flow reactor.

BACKGROUND AND PRIOR ART

Quinolones have broad spectrum of biological activity like antitumor, cannabinoid receptor modulation, anti-HIV-1 integrase, etc. More precisely 4-quinolone-3-carboxylic acid and its derivatives have been used as antibacterial agents such as ciprofloxacin, norfloxacin, lomefloxin, enrofloxacin, pefloxacin and danofloxacin for more than five decades. Very recently WHO approved fluroquinolone for the treatment tuberculosis (TB), and their use in multidrug-resistant (MDR)-TB due to the fact that they have a broad and potent spectrum of activity and can be administered orally. But all the reported methods suffer from harsh conditions such as high temperature (>200° C.), use of fancy reagents etc. Ivacaftor, also known as N-(2,4-di-tert-butyl-5-hydroxyphenyl)-1,4-dihydro-4-oxoquinoline-3-carboxamide, has the following formulas (IV and V):

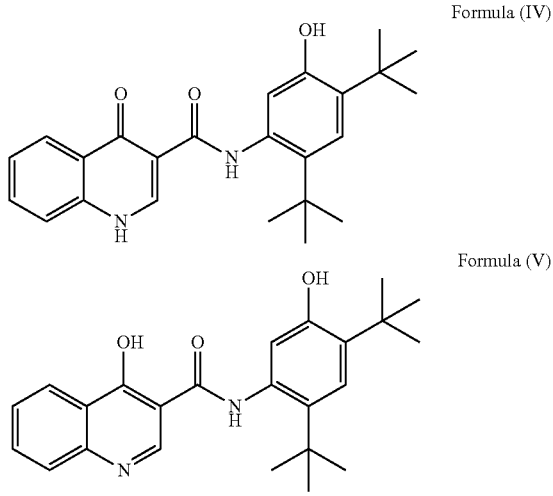

Ivacaftor was approved by FDA and marketed by vertex pharma for the treatment of cystic fibrosis under the brand name KALYDECO® in the form of 150 mg oral tablets. Kalydeco® is indicated for the treatment of cystic fibrosis in patients age 6 years and older who have a G55ID mutation in the CFTR (cystic fibrosis transmembrane conductance regulator) gene. Recently, FDA approved Orkambi®, a combination therapy for treatment of cystic fibrosis (CF). Orkambi is a combination of two categories of molecules, namely ivacaftor and Lumacaftor (known also as VX-809) both of which help in correcting the mutated genes in patients with cystic fibrosis.

WO2016181414 discloses a novel one pot two-step process for the synthesis of ivacaftor and related compounds of formula (I) and (II) its tautomers or pharmaceutically acceptable salts thereof starting from indole acetic acid amides.

Article titled "Breaking and Making of Rings: A Method for the Preparation of 4-Quinolone-3-carboxylic Acid Amides and the Expensive Drug Ivacaftor" by N Vasudevan et al. published in *Eur. J. Org. Chem.* 2015, pp 7433-7437 reports a simple and convenient method to access 4-quinolone-3-carboxylic acid amides from indole-3-acetic acid amides through one-pot oxidative cleavage of the indole ring followed by condensation.

WO2014118805 disclose a process for the preparation of ivacaftor and solvates thereof.

US patent application no. 2011064811 discloses a process for preparation of ivacaftor, which involves condensation of 4-oxo-1,4-dihydro-3-quinoline carboxylic acid with 5-amino-2,4-di-(tert-butyl)phenol in the presence of HBTU followed by the formation of ethanol crystalate, which is then treated with diethyl ether to yield ivacaftor as a solid.

US patent application no. 20100267768 discloses a process for preparation of ivacaftor, which involves the coupling of 4-oxo-1,4-dihydro-3-quinoline carboxylic acid with hydroxyl protected phenol intermediate in the presence of propyl phosphonic anhydride ($T_3P$®) followed by deprotection of hydroxyl protection group and optional crystallization with isopropyl acetate. The publication also discloses the use of highly expensive coupling reagent, propyl phosphonic anhydride; which in turn results to an increase in the manufacturing cost.

WO2014125506 and purity by using novel protected quinoline carboxylic acid compounds as intermediates. The present invention further encompasses a process for the preparation of ivacaftor using novel protected quinoline carboxylic acid compounds as intermediates.

US patent application no. 20110230519 discloses solid state forms of N-[2,4-bis(1,1-dimethylethyl)-5-hydroxyphenyl]-1,4-dihydro-4-oxoquinoline-3-carboxamide (Compound 1), pharmaceutical compositions thereof and methods therewith.

U.S. Pat. No. 7,495,103 discloses modulators of ATP-binding cassette transporters such as ivacaftor and a process for the preparation of modulators of ATP-binding cassette transporters such as quinoline compounds. The process includes condensation of 4-oxo-1,4-dihydro-3-quinoline carboxylic acid with aniline in presence of 2-(1H-7-azabenzotriazol-1-yl)-1,1,3,3-tetramethyluronium hexafluoro phosphate methanaminium (HATU) as shown:

The reported approaches for the synthesis of ivacaftor suffered from several drawbacks such as harsh conditions, high temperature reactions, carried out in batch mode and use of large excess of polyphosphoric acid and corrosive phosphoryl chloride. Furthermore, synthesis of ivacaftor requires use of high performance liquid chromatography (HPLC) techniques for the separation of ivacaftor and their analogues.

Therefore, it is the need to develop a short, mild, environmentally benign and convenient method for the preparation of ivacaftor. Accordingly, the present invention provides an improved process for the synthesis of ivacaftor which can be carried out in batch and continuous mode of synthesis.

OBJECTIVE OF THE INVENTION

The main objective of the present invention is to provide an improved process for the synthesis of ivacaftor starting from indole acetic acid ester at lower temperature.

Another objective of the present invention is to provide a continuous process for the synthesis of compound of formula (II) or formula (III) from compound of formula (I) in continuous flow reactor.

SUMMARY OF THE INVENTION

Accordingly, the present invention provides an improved process for the synthesis of ivacaftor comprising the steps of:
a) Subjecting ethyl ester of indole acetic acid to oxidative cleavage of indole moiety followed by adding reagent for Leimgruber-Batcho type cyclization and stirring the reaction mixture for the period in the range of 12 to 16 h at temperature in the range of 25 to 30° C. to afford ethyl 4-oxo-1,4-dihydroquinoline-3-carboxylate;
b) adding base to a suspension of Ethyl 4-oxo-1,4-dihydroquinoline-3-carboxylate of step (a) in solvent followed by heating the reaction mixture at temperature in the range of 80 to 90° C. for the period in the range of 12 to 16 h to afford 4-oxo-1,4-dihydroquinoline-3-carboxylic acid;
c) adding 5-amino-2,4-di-tert-butylphenol to the reaction mixture of 4-oxo-1,4-dihydroquinoline-3-carboxylic acid of step (b), a coupling agent in solvent followed by stirring the reaction mixture at temperature in the range of 25 to 30° C. for the period in the range of 14 to 16 h to afford ivacaftor.

In preferred embodiment, said oxidative cleavage of indole moiety is carried out by passing the $O_3$ stream to a solution of indole-3-acetic acid ester in solvent at −78° C. followed by adding $Me_2S$ to the cold reaction mixture and allowed to warm to temperature in the range of 25 to 30° C. for the period in the range of 6 to 8 h.

In another preferred embodiment, said oxidative cleavage of indole moiety is carried out by adding suspension of $NaIO_4$ in solvent to the reaction mixture of indole-3-acetic acid ester in solvent followed by allowing the reaction mixture to warm to temperature in the range of 25 to 30° C. for the period in the range of 10 to 12 h.

In yet another preferred embodiment, said solvent is selected from dichloromethane, tetrahydrofuran, ethanol, acetone, dimethylformamide, water or mixture thereof.

In still another preferred embodiment, said base in step (b) is an inorganic base and is selected from lithium hydroxide, sodium hydroxide, potassium hydroxide, barium hydroxide, tin hydroxide or mixture thereof.

In yet still another preferred embodiment, said coupling agent in step (c) is selected from HATU (1-[Bis(dimethylamino)methylene]-1H-1,2,3-triazolo[4,5-b]pyridinium 3-oxid hexafluoro phosphate), HBTU (O-Benzotriazole-N,N,N',N'-tetramethyl-uronium-hexafluoro-phosphate), hydroxybenzotriazole or (EDC) 1-Ethyl-3-(3-dimethylaminopropyl)carbodiimide, DCC (N,N'-Dicyclohexylcarbodiimide), or DIC (N,N'-Diisopropylcarbodiimide) or CDI (1,1'-Carbonyldiimidazole), TBTU (O-(Benzotriazol-1-yl)-N,N,N',N'-tetramethyluroniumtetrafluoroborate) or FDPP (Pentafluorophenyldiphenylphosphinate).

In yet still another preferred embodiment, said reagent for Leimgruber-Batcho type cyclization is selected from dialkylacetals of N,N-dimethylformamide like DMF-DMA, N,N-Dimethylformamide diethyl acetal, N,N-Dimethylformamidediisopropylacetal, N,N-Dimethylformamide di-tert-butyl acetal, Bredereck's reagent (tert-Butoxybis(dimethylamino)methane), Bis(dimethylamino)methoxymethane, Tris(dimethylamino)methane, alkyl orthoformate or triethylorthoformate.

In yet still another preferred embodiment, addition of said reagent for Leimgruber-Batcho type cyclization in step (a) is carried out at temperature in the range of 0 to 5° C.

In yet still another preferred embodiment, addition base in step (b) is carried out at temperature in the range of 0 to 5° C.

In another embodiment, the present invention provides a continuous process for the preparation of compound of formula (II) or formula (III);

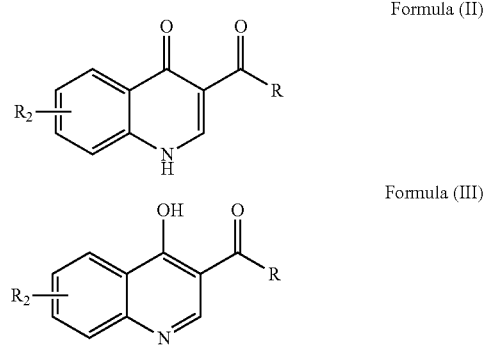

Formula (II)

Formula (III)

Wherein;
R is selected from the group consisting of hydrogen, alkyl, aryl, —$OR^1$ and —NR'R";
R' and R" are same or different and each is independently selected from the group consisting of hydrogen, alkyl, aryl, mono or di or tri substituted aryl wherein said substitutions are selected from the group consisting of alkyl or —$COOR^1$;
$R^1$ and $R^2$ are independently selected from the group consisting of hydrogen, halogen, alkyl and aryl.
comprising the steps of:
a) Passing the $O_3$ stream to the Tee junction containing indole-3-acetic acid ester of formula (I);

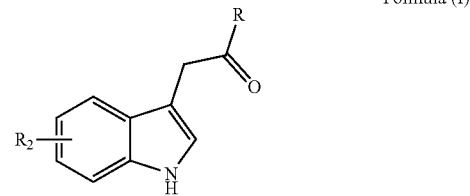

Formula (I)

Wherein R and $R^2$ are as defined above.
b) in solvent at temperature in the range of 0 to 5° C. in continuous flow reactor;
c) Pumping the reaction mixture in to a continuous stirred tank reactor containing solvent followed by Pumping the reaction mixture to a continuous layer separator for separation of two phases;
d) Pumping the solvent layer to another Tee junction containing DMF-DMA in solvent followed by pumping in continuous flow reactor to maintain the residence time in the range of 35 to 45 min to afford compound of formula (II).

In preferred embodiment, said compound of formula (I) is selected from Ethyl 2-(1H-indol-3-yl)acetate (1), 5-(2-(1H-indol-3-yl)acetamido)-2,4-di-tert-butylphenyl methyl carbonate (5).

In another preferred embodiment, said compound of formula (II) is selected from Ethyl 4-oxo-1,4-dihydroquinoline-3-carboxylate (2), N-(2,4-di-tert-butyl-5-hydroxyphenyl)-4-oxo-1,4-dihydroquinoline-3-carboxamide (4).

In yet another preferred embodiment, said process further comprises reacting N-(2,4-di-tert-butyl-5-hydroxyphenyl)-4-oxo-1,4-dihydroquinoline-3-carboxamide (4) with sodium methoxide in solvent in the next flow reactor and the residence time in the rage of 30 to 35 min to afford ivacaftor.

In still another preferred embodiment, said solvent is selected from methanol, water, 2-methyl tetrahydrofuran, ethyl acetate or mixture thereof.

DETAILED DESCRIPTION OF THE INVENTION

Figure 1:
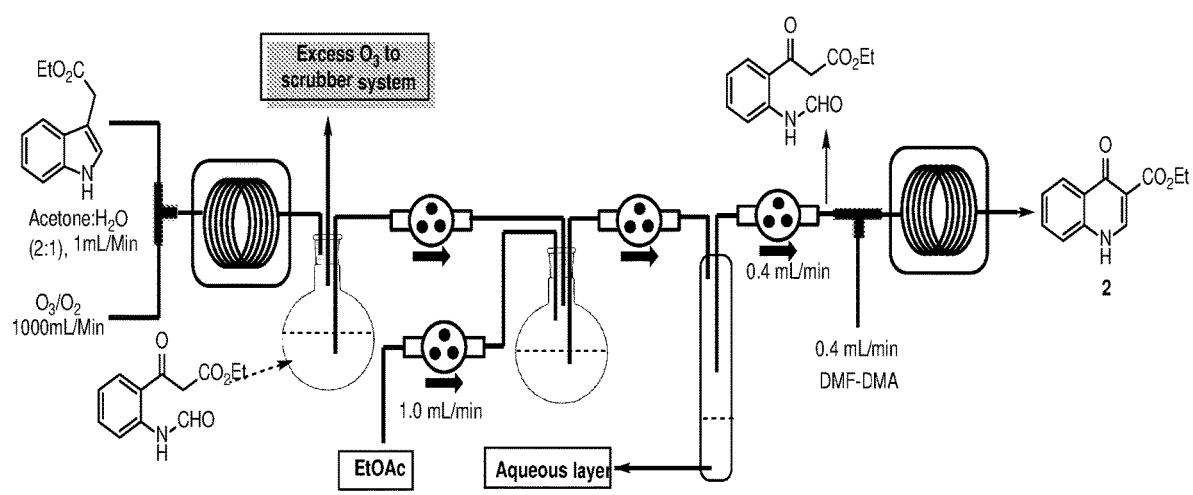
FIG. 1: Continuous flow process diagram for the synthesis of Ethyl 4-oxo-1,4-dihydroquinoline-3-carboxylate (2)
Figure 2:
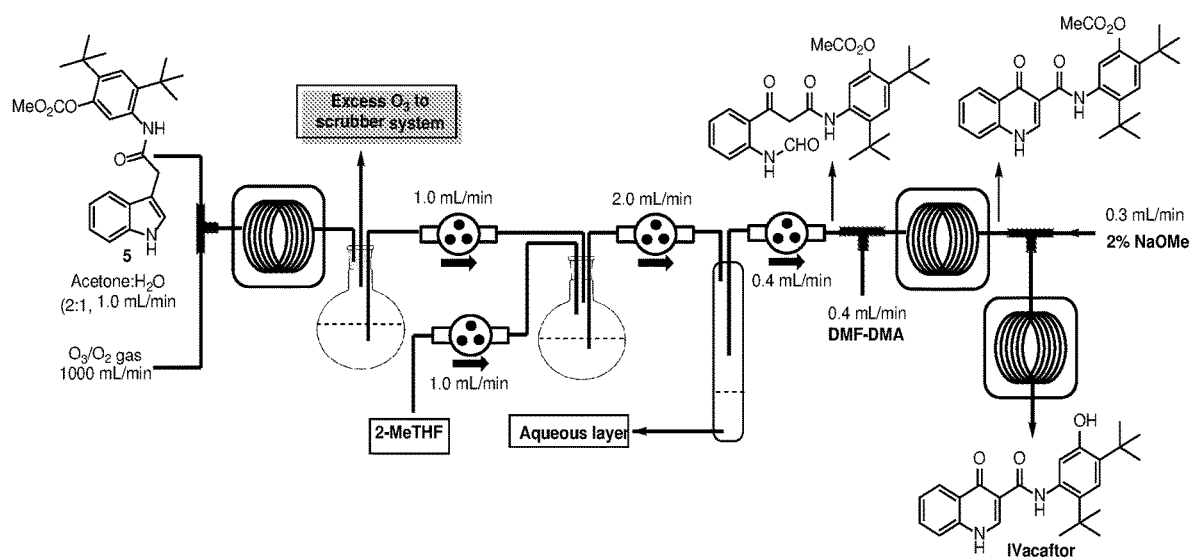
FIG. 2: Continuous flow process diagram for the synthesis of ivacaftor.

The invention will now be described in detail in connection with certain preferred and optional embodiments, so that various aspects thereof may be more fully understood and appreciated.

In the view of above, the present invention provides an improved process for the synthesis of ivacaftor and a continuous process for the preparation of compound of formula (II) or formula (III) from compound of formula (I).

In an embodiment, the present invention provides an improved process for the synthesis of ivacaftor comprising the steps of:
a) Subjecting ethyl ester of indole acetic acid to oxidative cleavage of indole moiety followed by adding reagent for Leimgruber-Batcho type cyclization and stirring the reaction mixture for the period in the range of 12 to 16 h at temperature in the range of 25 to 30° C. to afford ethyl 4-oxo-1,4-dihydroquinoline-3-carboxylate;
b) adding base to a suspension of Ethyl 4-oxo-1,4-dihydroquinoline-3-carboxylate of step (a) in solvent followed by heating the reaction mixture at temperature in the range of 80 to 90° C. for the period in the range of 12 to 16 h to afford 4-oxo-1,4-dihydroquinoline-3-carboxylic acid;
c) adding 5-amino-2,4-di-tert-butylphenol to the reaction mixture of 4-oxo-1,4-dihydroquinoline-3-carboxylic acid of step (b), a coupling agent in solvent followed by stirring the reaction mixture at temperature in the range of 25 to 30° C. for the period in the range of 14 to 16 h to afford ivacaftor.

In preferred embodiment, said oxidative cleavage of indole moiety is carried out by passing the O₃ (Ozone) stream to a solution of indole-3-acetic acid ester in solvent at −78° C. followed by adding Me₂S (Dimethyl sulfide) to the cold reaction mixture and allowed to warm to temperature in the range of 25 to 30° C. for the period in the range of 6 to 8 h.

In another preferred embodiment, said oxidative cleavage of indole moiety is carried out by adding suspension of NaIO₄ (Sodium periodate) in solvent to the reaction mixture of indole-3-acetic acid ester in solvent followed by allowing the reaction mixture to warm to temperature in the range of 25 to 30° C. for the period in the range of 10 to 12 h.

In yet another preferred embodiment, said solvent is selected from dichloromethane, tetrahydrofuran, ethanol, acetone, dimethylformamide, water or mixture thereof.

In still another preferred embodiment, said base in step (b) is an inorganic base and is selected from lithium hydroxide, sodium hydroxide, potassium hydroxide, barium hydroxide, tin hydroxide or mixture thereof.

In yet another preferred embodiment, said coupling agent in step (c) is selected from HATU (1-[Bis(dimethylamino)methylene]-1H-1,2,3-triazolo[4,5-b]pyridinium 3-oxid hexafluoro phosphate), HBTU (O-Benzotriazole-N,N,N',N'-tetramethyl-uronium-hexafluoro-phosphate), hydroxybenzotriazole or (EDC) 1-Ethyl-3-(3-dimethylaminopropyl)carbodiimide, DCC (N,N'-Dicyclohexylcarbodiimide), or DIC (N,N'-Diisopropylcarbodiimide) or CDI (1,1'-Carbonyldiimidazole), TBTU (O-(Benzotriazol-1-yl)-N,N,N',N'-tetramethyluroniumtetrafluoroborate) or FDPP (Pentafluorophenyldiphenylphosphinate).

In yet still another preferred embodiment, said reagent for Leimgruber-Batcho type cyclization is selected from dialkylacetals of N,N-dimethylformamide like DMF-DMA, N,N-Dimethylformamide diethyl acetal, N,N-Dimethylformamidediisopropylacetal, N,N-Dimethylformamide di-tert-butyl acetal, Bredereck's reagent (tert-Butoxybis(dimethylamino)methane), Bis(dimethylamino)methoxymethane, Tris(dimethylamino)methane, alkyl orthoformate or triethylorthoformate.

In yet still another preferred embodiment, addition of said reagent for Leimgruber-Batcho type cyclization in step (a) is carried out at temperature in the range of 0 to 5° C.

In yet still another preferred embodiment, addition base in step (b) is carried out at temperature in the range of 0 to 5° C.

The process for the synthesis of ivacaftor is as depicted in scheme 1:

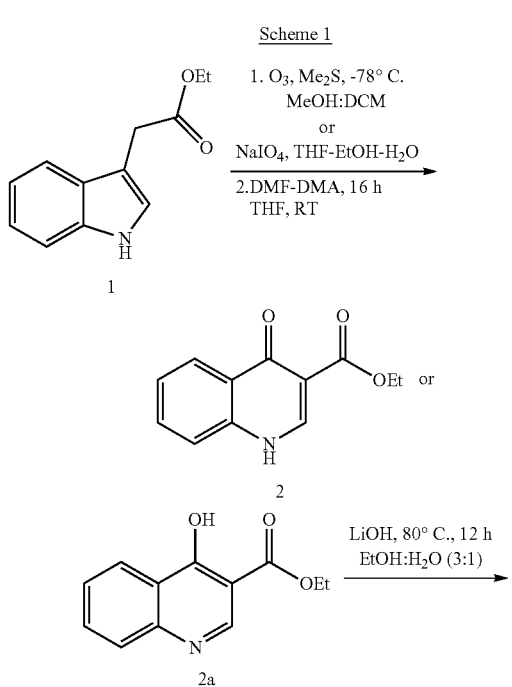

Scheme 1

-continued

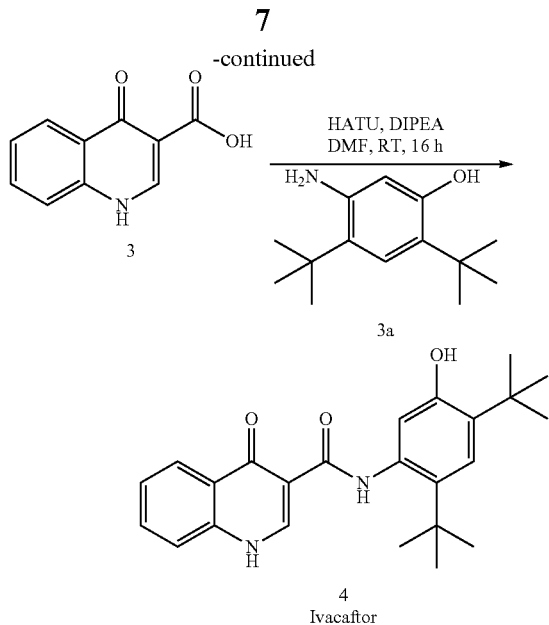

In another embodiment, the present invention provides a continuous process for the preparation of compound of formula (II) or formula (III);

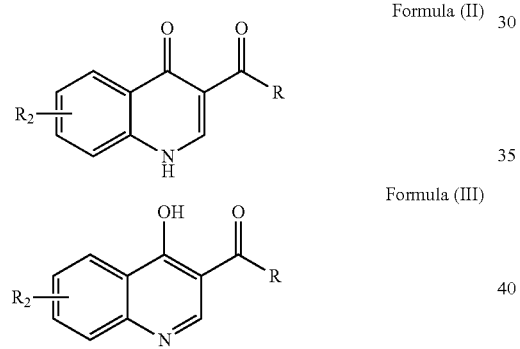

Wherein;
R is selected from the group consisting of hydrogen, alkyl, aryl, —OR$^1$ and —NR'R";
R' and R" are same or different and each is independently selected from the group consisting of hydrogen, alkyl, aryl, mono or di or tri substituted aryl wherein said substitutions are selected from the group consisting of alkyl or —COOR$^1$;
R$^1$ and R$^2$ is selected from the group consisting of hydrogen, halogen, alkyl and aryl.
comprising the steps of:
 a) Passing the O$_3$ stream to the Tee junction containing indole-3-acetic acid ester of formula (I);

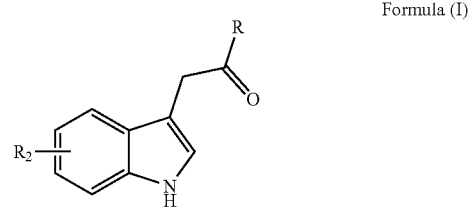

Wherein R and R$^2$ are as defined above.
 b) in solvent at temperature in the range of 0 to 5° C. in continuous flow reactor;
 c) Pumping the reaction mixture in to a continuous stirred tank reactor containing solvent followed by Pumping the reaction mixture to a continuous layer separator for separation of two phases;
 d) Pumping the solvent layer to another Tee junction containing DMF-DMA in solvent followed by pumping in continuous flow reactor to maintain the residence time in the range of 35 to 45 min to afford compound of formula (II).

In preferred embodiment, said compound of formula (I) is selected from Ethyl 2-(1H-indol-3-yl)acetate (1), 5-(2-(1H-indol-3-yl)acetamido)-2,4-di-tert-butylphenyl methyl carbonate (5).

In another preferred embodiment, said compound of formula (II) is selected from Ethyl 4-oxo-1,4-dihydroquinoline-3-carboxylate (2), N-(2,4-di-tert-butyl-5-hydroxyphenyl)-4-oxo-1,4-dihydroquinoline-3-carboxamide (4).

In yet another preferred embodiment, said process further comprises reacting N-(2,4-di-tert-butyl-5-hydroxyphenyl)-4-oxo-1,4-dihydroquinoline-3-carboxamide (4) with sodium methoxide in solvent in the next flow reactor and the residence time in the rage of 30 to 35 min to afford ivacaftor.

In still another preferred embodiment, said solvent is selected from methanol, water, 2-methyl tetrahydrofuran, ethyl acetate or mixture thereof.

The continuous process for the synthesis of compounds of formula (II) from formula (I) is as depicted in scheme 2:

Scheme 2

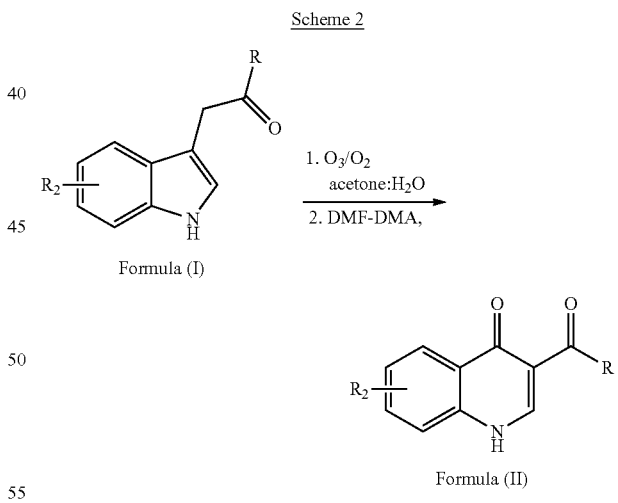

In an aspect, the present method is used for batch and continuous flow synthesis and is useful for synthesis of several quinolone based antibiotic drugs such as ciprofloxacin, norfloxacin etc.

The following examples, which include preferred embodiments, will serve to illustrate the practice of this invention, it being understood that the particulars shown are by way of example and for purpose of illustrative discussion of preferred embodiments of the invention.

EXAMPLES

Example 1: Synthesis of Ethyl 4-oxo-1,4-dihydroquinoline-3-carboxylate (2)

Method A:

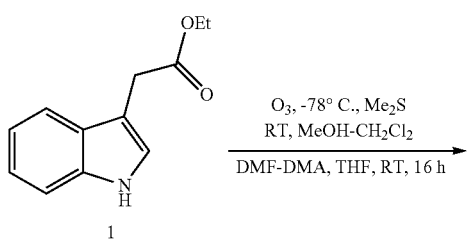

Indole-3-acetic acid ester (3 g, 14.77 mmol) was dissolved in CH$_2$Cl$_2$:MeOH (150 mL, 9:1), then a stream of O$_3$ was passed through the solution, at −78° C., until a blue color developed (15 min). The O$_3$ stream was continued for 4 min. Then surplus O$_3$ was removed by passing a stream of O$_2$ through the solution for 10 min or until the blue color completely vanished. Afterwards Me$_2$S (2.3 mL, 29.54 mmol) was added to the cold (−78° C.) mixture. The mixture was allowed to warm to room temperature for 8 h. Reaction mass was evaporated to dryness. This crude material, thus obtained was suspended in THF (15 mL), DMF-DMA (10.1 mL, 73.85 mmol) was added drop wise at 0° C., allowed to stir at room temperature for 18 h. Reaction mass was evaporated to dryness, cold H$_2$O (10 mL) was added, stirred for 30 min. The solid thus formed was filtered, washed with H$_2$O (50 mL) and dried to give desired compound as off white solid; (Yield: 1.44 g; 45%).

Method B:

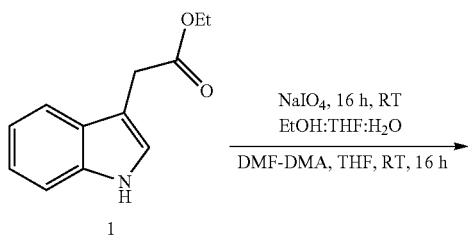

Indole-3-acetic acid ester 1 (1 g, 4.92 mmol) was dissolved in THF:EtOH:H$_2$O (15 mL, 1:1:1), then suspension of NaIO4 (5.23 g, 24.6 mmol) in H$_2$O (5 mL) was added drop wise at 0° C., The mixture was allowed to warm to room temperature for 12 h. Reaction mass filtered through filter paper, filtrate was evaporated to one third of its volume, extracted with EtOAc (3×15 mL). The combined organic layers were washed with H$_2$O (2×5 mL), dried over Na$_2$SO$_4$ and evaporated in vacuum. This crude material, thus obtained was suspended in THF (15 mL), DMF-DMA (3.69 mL, 24.6 mmol) was added drop wise at 0° C., allowed to stir at room temperature for 18 h. Reaction mass was evaporated to dryness, cold H$_2$O (50 mL) was added, stirred for 30 min. The solid thus formed was filtered, washed with H$_2$O (10 mL) and dried to give desired compound as off white solid; (Yield: 0.32 g; 30%).

Method C:

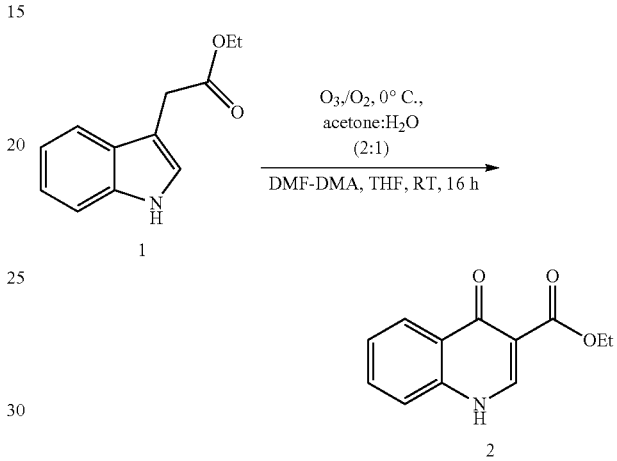

Indole-3-acetic acid ester (3 g, 14.77 mmol) was dissolved in acetone:water (100 mL, 3:1) and cooled to 0° C. Then a stream of O$_3$ was passed into the solution through bubbler until a blue color developed (20 min). Then excess of O$_3$ gas was removed by passing a stream of O$_2$ through the solution till the disappearance of the blue color. Afterwards reaction mass was extracted with DCM (3×50 mL), organic layer was washed with brine, dried over Na$_2$SO$_4$ and evaporated to dryness. This crude compound thus obtained above was suspended in THF (50 mL) and cooled to 0° C. DMF-DMA (10.1 mL, 73.85 mmol) was then added dropwise to the reaction mixture, and warned to room temperature for 18 h. Reaction mass was evaporated to dryness to give dark brown syrup. Then cold H$_2$O (75 mL) was added to reaction mass, stirred for 30 min. The solid thus formed was filtered, washed with H$_2$O (50 mL) and dried to give desired compound. (Yield: 1.3 g; 41%).

$^1$H NMR (200 MHz, DMSO-d$_6$) δ=1.28 (t, J=7.07 Hz, 3H) 4.22 (q, J=7.16 Hz, 2H) 6.93-7.51 (m, 1H) 7.54-7.79 (m, 2H) 8.16 (dd, J=8.02, 0.95 Hz, 1H) 8.56 (s, 1H) 12.32 (brs, 1H) MS: 218 (M+Na)$^+$.

Example 2: Synthesis of 4-Oxo-1,4-dihydroquinoline-3-carboxylic acid (3)

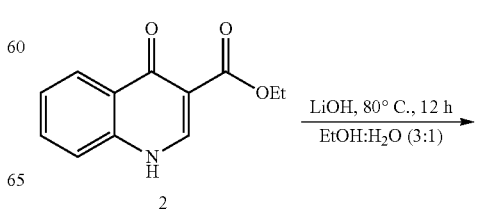

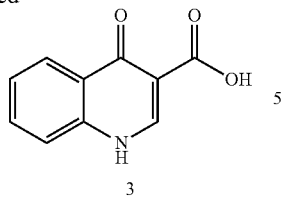

To a suspension of ethyl 4-oxo-1,4-dihydroquinoline-3-carboxylate (2) (0.5 g, 2.30 mmol) in THF (10 mL), a solution of aqueous 1 M LiOH (aq) (4.60 mL, 4.60 mmol) was added drop wise at 0° C., and then the reaction mixture was heated at 80° C. for 16 h. Reaction mass was evaporated to dryness, dissolved in $H_2O$ (5 mL), washed with diethyl ether (2×5 mL). The aqueous layer was acidified with 1 M HCl (aq), compound thus precipitated was filtered, dried under vacuum to give desired compound as off-white solid. Yield: (0.35 g; 80%) $^1$H NMR (400 MHz, DMSO-d6) δ=15.36 (brs, 1H), 13.43 (brs, 1H), 8.91 (s, 1H), 8.31 (d, J=8.3 Hz, 1H), 7.98-7.75 (m, 2H), 7.62 (t, J=7.6 Hz, 1H).

Examples: 3: Synthesis of Ivacaftor (4)

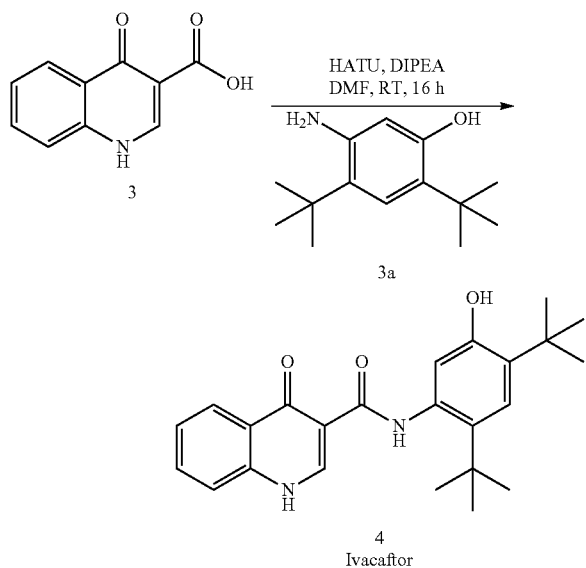

A mixture of 4-oxo-1,4-dihydroquinoline-3-carboxylic acid 3 (0.25 g, 1.32 mmol), N,N-diisopropylethylamine (0.97 mL, 5.38 mmol), and HATU (1.01 g, 2.64 mmol) in DMF (5 mL) was stirred at 25° C. for 10 min and then 5-amino-2,4-di-tert-butylphenol 3a (0.58 g, 2.64 mmol) was added in one portion, allowed to stir for 12 h. The reaction mass was extracted with EtOAc (2×10 mL). Combined organic layers were washed with $H_2O$ (5 mL), saturated $NaHCO_3$ solution (5 mL), $H_2O$ (5 mL), brine (5 mL), dried over anhydrous $Na_2SO_4$ and evaporated to dryness. crude residue was purified by silica gel chromatography (2-3% MeOH-DCM) to give off-white solid, which on further crystallization in EtOH gave desired compound as white solid (0.23 g, 46%).

$^1$H NMR (500 MHz, DMSO-d6) δ=12.88 (brs, 1H), 11.82 (brs, 1H), 9.20 (brs, 1H), 8.87 (brs, 1H), 8.33 (d, J=6.9 Hz, 1H), 7.88-7.68 (m, 2H), 7.52 (brs, 1H), 7.17 (brs, 1H), 7.11 (brs, 1H), 1.38 (d, J=7.6 Hz, 18H).

Experimental Procedure: (Continues Process)

Example 4: Synthesis of Ethyl 4-oxo-1,4-dihydroquinoline-3-carboxylate (2)

Indole-3-acetic acid ester 1 (3 g, 14.77 mmol) was dissolved in acetone:water (50 mL, 2:1), and loaded in syringe. Pump is used to pump this solution in syringe to a Tee junction where other inlet of Tee junction was connected to ozone generator where stream of $O_3$ was passed to the Tee junction at 0° C. Outlet of Tee junction was connected to the continuous flow reactor where reaction takes place. Outlet of the flow reactor is connected to 2-neck round bottom flask. Flow rate of substrate 1 (1.0 mL/min) and $O_3/O_2$ (1000 mL/min) gas was kept to have 2 sec residence time for overall reaction. One neck is used to evacuate excesses $O_3$ for quenching and from other neck product was transferred to the other round bottom flask under stirring where water (0.1 mL/min) and ethyl acetate (1.0 mL) was pumped. The mixed solution was then pumped to the separating funnel for layer separation. Ethylacetate layer was then pumped (0.4 mL/min) to another Tee junction where other inlet of Tee junction was connected to the syringe filled with DMF-DMA in ethylacetate (0.4 mL/min; 10% v/v). Outlet of Tee connected to the continuous flow reactor to maintain the 40 min residence time. Reaction mass, collected from at the outlet of the flow reactor, was evaporated to give dark brown syrup. This crude material was added dropwise into cold $H_2O$ (75 mL) under stirring. The precipitates thus formed were filtered, washed with $H_2O$ (50 mL), dried to give off-white solid (yield: 1.56 g; 54%)

Example 5: Synthesis of N-(2,4-di-tert-butyl-5-hydroxyphenyl)-4-oxo-1,4-dihydroquinoline-3-carboxamide (4) and synthesis of ivacaftor 5-(2-(1H-indol-3-yl)acetamido)-2,4-di-tert-butylphenyl methyl carbonate 5 (0.75 g, 1.72 mmol) was dissolved in acetone:water (50 mL, 2:1), and loaded in syringe. Pump is used to pump this solution in syringe to a Tee junction where other inlet of Tee junction was connected to ozone generator where stream of $O_3$ was passed to the Tee junction at 0° C. Outlet of Tee junction was connected to the continuous flow reactor where reaction takes place. Outlet of the flow reactor is connected to 2-neck round bottom flask. Flow rate of substrate 5 (1.0 mL/min) and $O_3/O_2$ (1000 mL/min) gas was kept to have 2 sec residence time for overall reaction. One neck is used to evacuate excesses $O_3$ for quenching and from other neck product was transferred to the other round bottom flask under stirring where water (0.1 mL/min) and 2-MeTHF (1.0 mL) was pumped. The mixed solution was then pumped to the separating funnel for layer separation. 2-MeTHF layer was then pumped (0.4 mL/min) to another Tee junction where other inlet of Tee junction was connected to the syringe filled with DMF-DMA in 2-MeTHF (0.4 mL/min; 10% v/v). Outlet of Tee connected to the continuous flow reactor to maintain the 40 min residence time.

Outlet of the flow reactor is connected to other Tee junction, which is already connected to other inlet with sodium methoxide in methanol (0.3 mL/min; 2% w/v) solution and the next flow reactor to maintain the residence time of (35 min) and product was collected at the outlet of the flow reactor. The solution collected at outlet was washed with cold 1N HCl (3 mL×2), brine solution (5 mL), dried over Na2SO4 and evaporated to dryness. This crude material was subjected to purification by column chromatography (silica gel 230-400 mesh; 0.3:0.7:MeOH:DCM) to offer desired compound as of white solid (yield: 0.45 g; 60%)

Advantages of Invention

1. Short, mild and suitable for large scale production as well as on the spot synthesis.
2. Present method features ozonolytic as well as non-ozonolytic way for oxidative cleavage of indole moiety and one pot quadrupole reaction for the construction of quinolone core.
3. Involves only one purification step.
4. Present method is suitable for continuous flow synthesis.
5. Could be applied for synthesis of several quinolone based antibiotic drugs.

The invention claimed is:
1. An improved process for the synthesis of ivacaftor comprising the steps of:
   a) subjecting an ethyl ester of indole acetic acid to oxidative cleavage of indole moiety followed by adding a reagent for typo cyclization and stirring the reaction mixture for the period in the range of 12 to 16 h at temperature in the range of 25 to 30° C. to afford ethyl 4-oxo-1,4-dihydroquinoline-3-carboxylate (2);
   b) adding a base to a suspension of Ethyl 4-oxo-1,4-dihydroquinoline-3-carboxylate of step (a) in solvent followed by heating the reaction mixture at temperature in the range of 80 to 90° C. for the period in the range of 12 to 16 h to afford 4-oxo-1,4-dihydroquinoline-3-carboxylic acid (3); and
   c) adding 5-amino-2,4-di-tert-butylphenol to the reaction mixture of 4-oxo-1,4-dihydroquinoline-3-carboxylic acid of step (b), a coupling agent in solvent followed by stirring the reaction mixture at temperature in the range of 25 to 30° C. for the period in the range of 14 to 16 h to afford the ivacaftor (4).
2. The process according to claim 1, wherein the oxidative cleavage of indole moiety is carried out by passing an $O_3/O_2$ stream to a solution of indole-3-acetic acid ester in solvent at −78° C. followed by adding $Me_2S$ to the cold reaction mixture and allowed to warm to temperature in the range of 25 to 30° C. for the period in the range of 6 to 8 h.
3. The process according to claim 1, wherein the oxidative cleavage of indole moiety is carried out by adding suspension of $NaIO_4$ in solvent to the reaction mixture of indole-3-acetic acid ester in solvent followed by allowing the reaction mixture to warm to temperature in the range of 25 to 30° C. for the period in the range of 10 to 12 h.
4. The process according to claim 1, wherein the solvent is selected from dichloromethane, tetrahydrofuran, ethanol, acetone, dimethylformamide, water or mixture thereof.
5. The process according to claim 1, wherein the base in step (b) is an inorganic base and is selected from lithium hydroxide, sodium hydroxide, potassium hydroxide, barium hydroxide, tin hydroxide or mixture thereof.
6. The process according to claim 1, wherein the coupling agent in step (c) is selected from HATU (1-[Bis(dimethylamino)methylene]-1H-1,2,3-triazolo[4,5-b]pyridinium 3-oxid hexafluoro phosphate), HBTU (O-Benzotriazole-N,N,N',N'-tetramethyl-uronium-hexafluoro-phosphate),hydroxybenzotriazole or (EDC) 1-Ethyl-3-(3-dimethylamino-propyl)carbodiimide, DCC (N,N'-Dicyclohexylcarbodiimide), or DIC (N,N'-Diisopropylcarbodiimide) or CDI (1,1'-Carbonyldiimidazole), TBTU (O-(Benzotriazol-1-yl)-N,N, N',N'-tetramethyluroniumtetrafluoroborate) or FDPP (Pentafluorophenyldiphenylphosphinate).
7. The process according to claim 1, wherein the reagent for cyclization is selected from dialkylacetals of N,N-dimethylformamide, Bredereck's reagent (tert-Butoxybis(dimethylamino)methane), Bis(dimethylamino)methoxymethane, Tris(dimethylamino)methane, alkyl orthoformate or triethylorthoformate; wherein the dialkylacetals of N,N-dimethylformamide are selected from Dimethyl formamidedimethy acetal (DMF-DMA), N,N-Dimethylformamide diethyl acetal, N,N-Dimethylformamidediisopropylacetal and N,N-Dimethylformamide di-tert-butyl acetal.
8. The process according to claim 1, wherein the addition of the reagent for cyclization in step (a) is carried out at temperature in the range of 0 to 5° C.
9. The process according to claim 1, wherein addition of the base in step (b) is carried out at temperature in the range of 0 to 5° C.
10. A continuous process for the preparation of compound of formula (II) or formula (III);

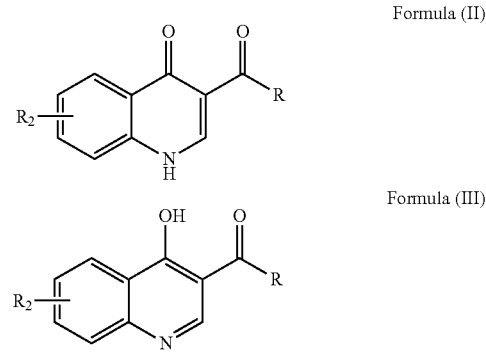

wherein,
R is selected from the group consisting of hydrogen, alkyl, aryl, $OR^1$ and —NR'R";
R' and R" are same or different and each is independently selected from the group consisting of hydrogen, alkyl, aryl, mono or di or tri substituted aryl wherein said substitutions are selected from the group consisting of alkyl or —$COOR^1$;
$R^1$ and $R^2$ are selected from the group consisting of hydrogen, halogen, alkyl and aryl;
the continuous process comprising the steps of:
   a) passing an $O_3$ stream to a Tee junction containing indole-3-acetic acid ester of formula (I),

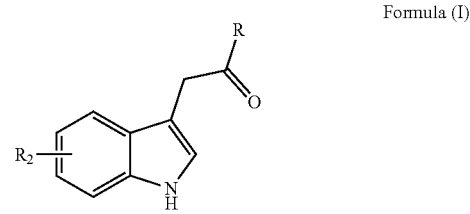

wherein R and $R^2$ are as defined above,
   in a solvent at a temperature in the range of 0 to 5° C. in a continuous flow reactor.
   b) pumping the reaction mixture in to a continuous stirred tank reactor containing solvent followed by pumping the reaction mixture to a continuous layer separator for separation of two phases;

c) pumping the solvent layer to another Tee junction containing DMF-DMA in solvent followed by pumping in continuous flow reactor to maintain the residence time in the range of 35 to 45 min to afford the compound of formula (II).

11. The process according to claim 10, wherein the compound of formula (I) is selected from Ethyl 2-(1H-indol-3-yl)acetate (1), 5-(2-(1H-indol-3-yl)acetamido)-2,4-di-tert-butylphenyl methyl carbonate (5).

12. The process according to claim 10, wherein the compound of formula (II) is selected from Ethyl 4-oxo-1,4-dihydroquinoline-3-carboxylate (2), N-(2,4-di-tert-butyl-5-hydroxyphenyl)-4-oxo-1,4-dihydroquinoline-3-carboxamide (4).

13. The process according to claim 10, wherein the process further comprises reacting N-(2,4-di-tert-butyl-5-hydroxyphenyl)-4-oxo-1,4-dihydroquinoline-3-carboxamide (4) with sodium methoxide in solvent in the next flow reactor and the residence time in the range of 30 to 35 min to afford ivacaftor.

14. The process according to claim 10, wherein the solvent is selected from methanol, water, 2-methyl tetrahydrofuran, ethyl acetate or mixture thereof.

15. The process according to claim 13, wherein the solvent is selected from methanol, water, 2-methyl tetrahydrofuran, ethyl acetate or mixture thereof.

16. The process according to claim 7, wherein the oxidative cleavage of indole moiety is carried out by passing an $O_3/O_2$ stream to a solution of indole-3-acetic acid ester in solvent at −78° C. followed by adding $Me_2S$ to the cold reaction mixture and allowed to warm to temperature in the range of 25 to 30° C. for the period in the range of 6 to 8 h.

17. The process according to claim 7, wherein the oxidative cleavage of indole moiety is carried out by adding suspension of $NaIO_4$ in solvent to the reaction mixture of indole-3-acetic acid ester in solvent followed by allowing the reaction mixture to warm to temperature in the range of 25 to 30° C. for the period in the range of 10 to 12 h.

18. The process according to claim 1, wherein the reagent for cyclization is selected from Dimethyl formamidedimethy acetal (DMF-DMA), N,N-Dimethylformamide diethyl acetal, N,N-Dimethylformamidediisopropylacetal and N,N-Dimethylformamide di-tert-butyl acetal.

* * * * *